| United States Patent [19] | [11] | 4,375,477 |
|---|---|---|
| Bey et al. | [45] | Mar. 1, 1983 |

[54] FLUORINATED METHYL BETA-ALANINE DERIVATIVES

[75] Inventors: Philippe Bey, Strasbourg; Michael Jung, Illkirch-Graffenstaden, both of France; Fritz Gerhart, Willstaett, Fed. Rep. of Germany

[73] Assignee: Merrell Toraude et Compagnie, France

[21] Appl. No.: 170,396

[22] Filed: Jul. 21, 1980

[30] Foreign Application Priority Data

Jul. 26, 1979 [GB] United Kingdom ............. 7926030
Jan. 25, 1980 [GB] United Kingdom ............. 8002553

[51] Int. Cl.$^3$ ................. C07C 101/10; A61K 31/195
[52] U.S. Cl. ............................. 424/319; 424/305; 424/320; 560/39; 560/41; 560/161; 560/190; 560/192; 560/227; 560/172; 562/448; 562/449; 562/561; 564/197; 564/198; 564/509

[58] Field of Search ............. 562/574, 561; 560/172, 560/161, 41, 137; 260/239 AL; 564/155, 159, 197, 198; 424/300, 308, 311, 319, 320, 244

[56] References Cited

U.S. PATENT DOCUMENTS 4,264,590 4/1981 Chu ............................. 562/574

FOREIGN PATENT DOCUMENTS 47-32966 8/1972 Japan ........................... 560/172
2005264 4/1979 United Kingdom .

*Primary Examiner*—Michael L. Shippen
*Attorney, Agent, or Firm*—David E. Frankhouser; Raymond A. McDonald; William J. Stein

[57] ABSTRACT

Beta-monofluoromethyl beta-alanine, beta-difluoromethyl beta-alanine and pharmaceutically acceptable esters and amides derived from the acid group, amides derived from the amine group, and salts thereof are novel compounds which inhibit γ-aminobutyric acid transaminase (GABA-T).

9 Claims, No Drawings

FLUORINATED METHYL BETA-ALANINE DERIVATIVES

FIELD OF INVENTION

This invention relates to novel pharmaceutically useful fluorinated methyl beta-alanine derivatives and related compounds which are inhibitors of γ-aminobutyric acid transaminase (GABA-T). The invention provides the compounds per se, pharmaceutical compositions comprising said compounds, methods of medical treatment using said compounds and processes for preparing said compounds.

BACKGROUND OF INVENTION

Several previous studies have shown that γ-aminobutyric acid (GABA) is a major inhibitory transmitter of the central nervous system and that disturbance of the excitation and inhibition interplay can lead to disease states such as Huntington's chorea, Parkinsonism, schizophrenia, epilepsy, depression, hyperkinesis and manic depression disorders. Certain compounds are known to be irreversible inhibitors of GABA-T and thereby to elevate brain levels of GABA, for example fluorinated methyl γ-aminobutyric and δ-aminopentanoic acids and certain derivatives thereof as described in U.K. Patent Specification No. 2005264A.

European Patent Application No. 78100059.1 discloses inter alia γ-monofluoromethyl-γ-aminobutyric acid and pharmaceutically acceptable acid addition salts thereof. It is stated in said European Patent Application that the said compound inhibits glutamic acid decarboxylase and displays CNS activities, including sedative and antidepressant indications.

The compounds 4,4,4-trifluoro-3-amino-1-butanoic acid (i.e. beta-trifluoromethyl beta-alanine) and 4,4,4-trifluoro-3-amino-1-butyramide (i.e. beta-trifluoromethyl beta-alanine primary amide) have been reported in the literature (see, for example, H. M. Walborsky et al, J. Org. Chem. 21 (1956) at pages 538–539). As far as we are aware, no pharmacological activity has been reported for these known fluorinated methyl beta-alanine derivatives.

SUMMARY OF INVENTION

The compounds of the present invention are beta-monofluoromethyl beta-alanine, beta-difluoromethyl beta-alanine and pharmaceutically acceptable esters and amides derived from the acid group and amides derived from the amine group, and salts thereof.

Individual optical isomers of the compounds of general Formula I are also included within the scope of this invention.

The compounds of the invention are useful pharmacological agents in that said compounds are irreversible inhibitors of GABA-T. Certain of the compounds of general Formula I are also useful as intermediates in the preparation of useful pharmacological agents.

The compounds of the invention have a surprising activity in that they are significantly more active irreversible inhibitors of GABA-T than the analogous fluorinated methyl γ-aminobutyric and δ-aminopentanoic acids and derivatives described in U.K. Patent Specification No. 2005264A whereas 4,4,4-trifluoro-3-amino-1-butanoic acid is apparently devoid of such activity.

DETAILED DESCRIPTION OF INVENTION

It is preferred that the esters of the invention are $C_1$–$C_8$ alkyl esters. It is also preferred that the amides of the invention are primary amides, $C_1$–$C_4$ alkyl amides, di($C_1$–$C_4$ alkyl) amides or an amide derived from an L-aminocarboxylic acid, especially a naturally occurring aminocarboxylic acid. In the case of the amino derivatives, it is preferred that the N-substituent group is $C_2$–$C_5$ alkylcarbonyl, phenylcarbonyl, phenyl-($C_1$–$C_4$ alkyl)-carbonyl, or an acyl group derived from an L-aminocarboxylic acid, especially a naturally occurring aminocarboxylic acid.

Preferably, the compounds of the invention are those represented by the following general Formula I:

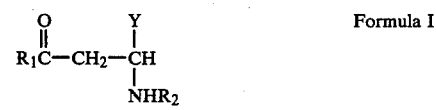

Formula I

In the above general Formula I:

Y is $FCH_2$—, or $F_2CH$—;

$R_1$ is hydroxy, $C_1$–$C_8$ alkoxy, —$NR_3R_4$ wherein $R_3$ and $R_4$ independently represent hydrogen or $C_1$–$C_4$ alkyl, or an aminocarboxylic acid residue derived by removal of a hydrogen atom from the amino moiety of an L-aminocarboxylic acid;

$R_2$ is hydrogen, $C_2$–$C_5$ alkylcarbonyl, $C_2$–$C_5$ phenyl-carbonyl, phenyl-($C_1$–$C_4$ alkyl)-carbonyl, or an aminocarboxylic acid residue derived by removal of an hydroxy group from the carboxy moiety of an L-aminocarboxylic acid;

Reference in this Specification, including the Claims to an alkyl group or moiety means a straight or branched chain alkyl group or moiety and, in the case of an alkyl group or moiety having structural isomers, includes all of those isomers and mixtures thereof unless a particular isomer is specified or clearly implied by the context.

Illustrative examples of straight or branched alkyl groups or moieties having from 1 to 4 carbon atoms as used herein are methyl, ethyl, n-propyl, isopropyl and n-butyl.

Illustrative examples of straight or branched alkoxy groups having from 1 to 8 carbon atoms as used herein are methoxy, ethoxy, isopropoxy, n-butoxy, n-pentyloxy, tert-pentyloxy, n-hexyloxy and n-octyloxy.

When $R_1$ is an aminocarboxylic acid residue, it is preferably of the formula —$NHCH(R_5)CO_2H$, wherein $R_5$ is hydrogen, $C_1$–$C_4$ alkyl, benzyl or p-hydroxybenzyl. Similarly, when $R_2$ is an aminocarboxylic acid residue, it is preferably of the formula —$COCH(R_5)NH_2$ wherein $R_5$ is as defined above. Examples of aminocarboxylic acids from which said preferred residues are derived include glycine, alanine, valine, leucine, isoleucine, phenylalanine and tyrosine.

Illustrative examples of pharmaceutically acceptable salts of the compounds of this invention include non-toxic acid addition salts formed with inorganic acids, such as hydrochloric, hydrobromic, sulfuric and phosphoric acid, and organic acids, such as, methane sulfonic, salicyclic, maleic, malonic, tartaric, citric and ascorbic acids; and non-toxic salts formed with inorganic or organic bases, such as, hydroxides of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, methylaminoethanol, ethanolamine and piperidine. The salts are prepared by conventional means.

Particularly preferred compounds of this invention are those of general Formula I wherein $R_2$ is $C_2$–$C_5$ alkylcarbonyl or, especially, hydrogen. In another preferred embodiment of this invention $R_1$ in general Formula I is $C_1$–$C_8$ alkoxy or especially, hydroxy. Further compounds of general Formula I wherein Y is $F_2CH-$ are preferred to those in which Y is $FCH_2-$. The most preferred compounds of this invention are those of general Formula I wherein $R_1$ is hydroxy, $R_2$ is hydrogen.

Illustrative examples of compounds of general Formula I are the following:
3-amino-3-monofluoromethylpropionic acid (otherwise β-monofluoromethyl-β-alanine or 4-fluoro-3-amino-1-butanoic acid),
3-amino-3-difluoromethylpropionic acid (otherwise β-difluoromethyl-β-alanine or 4,4-difluoro-3-amino-1-butanoic acid),
3-amino-3-monofluoromethylpropionamide,
3-amino-3-difluoromethyl-N,N-dimethyl-propionamide,
3-amino-3-monofluoromethyl-N-ethyl-propionamide,
ethyl 3-amino-3-monofluoromethylpropionate,
isopropyl 3-amino-3-difluoromethylpropionate,
2-(3'-amino-3'-difluoromethyl-1'-oxo-propylamino) acetic acid,
3-difluoromethyl-3-(1'-oxo-ethylamino)propionic acid,
methyl 3-monofluoromethyl-3-(aminomethylcarbonylamino)-propionate,
3-monofluoromethyl-3-(benzoylamino)propionic acid,
3-difluoromethyl-3-(phenylpropionylamino) propionic acid.

The compounds of the invention are useful as inhibitors of GABA-T resulting in an increase in brain levels of GABA rendering the compounds useful in the treatment of disorders of the central nervous system (CNS) function characterised in a low level of brain GABA, for example, seizure disorders associated with epilepsy. They are also indicated for use in other so characterised CNS disorders consisting of involuntary movement for example those associated with Parkinsonism, extrapyramidal effects of drugs, for example, neuroleptics, alcohol withdrawal, barbiturate withdrawal, psychoses associated with schizophrenia, depression, manic depression and hyperkinesis. The compounds of the invention are also useful as hypothermic agents, myorelaxants, cholinergic agents, antibacterial agents, anticonvulsive agents, analgesics, anorexigenic agents, antiobesity agents, tranquilizers, sedatives and central nervous system stimulants.

The ability of the compounds of the invention to inhibit GABA-T may be shown by the protective effect administration of the compound has on audiogenic seizures in mice of the DBA strain measured by the general method described by Simler et al., Biochem. Pharmacol. 22, 1701 (1973) which is currently used to evidence antiepileptic activity. The inhibition of GABA-T may also be shown by the methods of M. J. Jung et al (J. Neurochemistry, 28 (1977) 717–723) and C. Lamar (J. Neurochemistry, 17 (1970) 165–170).

The compounds of this invention can be administered in various manners to achieve the desired effect. The compounds can be administered alone or in the form of pharmaceutical preparations to the patient being treated either orally or parenterally, for example, subcutaneously, intravenously or interperitoneally. The amount of novel compound administered will vary and can be any effective amount. Depending upon the patient, the condition being treated and the mode of administration, the quantity of novel compound administered may vary over a wide range to provide from about 0.1 mg/kg (milligram per kilogram) to about 50 mg/kg of body weight of the patient per day. Unit doses of these compounds can contain, for example, from about 5 mg to 2000 mg of the compounds and may be administered, for example, from 1 to 4 times daily.

As used herein the term patient is taken to mean warm blooded animals, such as, mammals, for example, cats, dogs, rats, mice, guinea pigs, sheep, horses, bovine cows and humans.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Some examples of such diluents or carriers are lactose, dextrose, sucrose, sorbitol, mannitol, starches, gum acacia, calcium phosphate, liquid paraffin, cocoa butter, oil of theobroma, alginates, tragacanth, gelatin, syrup B.P., methyl cellulose, polyoxyethylene sorbitan monolaurate, methyl- and propyl-hydroxybenzoate, talc, magnesium stearate or mineral oil.

The formulations of the invention may be adapted for enteral or parenteral use and may be administered to the patient in the form of tablets, capsules, suppositories, solutions, suspensions or the like.

The solid unit dosage forms can be of the conventional type. Thus, the solid form can be a capsule which can be of the ordinary gelatin type containing an active compound of this invention and a carrier, for example, lubricant and inert fillers, such as, lactose, sucrose and corn starch. In another embodiment, the novel compounds are tableted with conventional tablet bases such as lactose, sucrose or corn starch in combination with binders, such as, acacia, corn starch or gelatin, disintegrating agents, such as, corn starch, potato starch or alginic acid and a lubricant such as stearic acid or magnesium stearate.

For parenteral administration the compounds may be administered as injectable dosages of a solution or suspension of a compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related solutions, ethanols and glycols, such as, propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials, such as, biodegradable polymers or synthetic silicones, for example, Silastic, silicone rubber manufactured by the Dow-Corning Corporation.

In the specific examples included hereinbelow illustrative examples of suitable pharmaceutical formulations are described.

Beta-monofluoromethyl beta-alanine, beta-difluoromethyl beta-alanine and salts thereof can be prepared by oxidation in manner known per se of a corresponding 1-fluorinated-2-amino-4-pentene in which the amino group is protected by a suitable blocking group to form the corresponding 4-fluorinated-3-protected amino-1-butanoic acid and subsequently removing the blocking group in manner known per se to free the amino group or form an acid salt thereof. These reaction steps can be represented as follows:

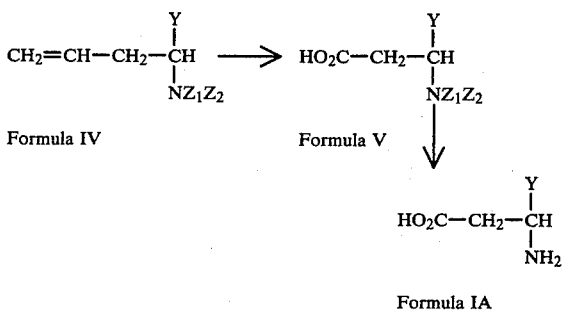

In Formulae IA, IV and V, Y is $FCH_2-$ or $F_2CH-$ and in Formulae IV and V, $Z_1$ is hydrogen or a subsequently removable blocking group and $Z_2$ is a subsequently removable blocking group or $Z_1$ and $Z_2$ together represent a subsequently removable divalent blocking group. Suitably, the oxidation can be carried out using potassium permanganate, maganese dioxide, chromium trioxide, potassium dichromate, osmium tetroxide or ruthenium tetroxide in a solvent such as water, acetic acid, ethanol, acetone, pyridine, carbon tetrachloride, methylene chloride, diethylether, benzene or cyclohexane. The oxidation can be performed at a temperature in the range 0° C. to the boiling point of the respective solvent and for a period in the range 5 minutes to 48 hours. Preferably, the oxidation is carried out with potassium permanganate in aqueous acetic acid at room temperature overnight.

The 4-fluorinated-3-protected amino-1-butanoic acid of Formula 1A can be isolated from the oxidation reaction product by removal of the solvent under vacuum followed by addition of water and extraction with ether or chloroform.

The blocking group suitably can be acyl, alkoxycarbonyl, carbobenzoxy, benzenesulfonyl or tosyl and preferably is tert-butoxycarbonyl or benzenesulfonyl. Both amino hydrogen atoms can be substituted by a blocking group such as phthalyl. The blocking groups are introduced in manner known per se by, for example, reaction of the amine with an acylchloride, anhydride, sulfonylchloride or tert-butyloxycarbonyloxyimino-2-phenylacetonitrile (BOC-ON). The preferred blocking groups tert-butoxycarbonyl and benzenesulfonyl are introduced with BOC-ON and benzenesulfonylchloride, respectively, in the presence of a base.

Removal of the blocking group after the oxidation step is performed in manner known per se for the relevant blocking group. Usually, said removal will be by hydrolytic cleavage using a strong organic or mineral acid; by catalytic hydrogenation using Pd or Pt catalyst; or by hydrogen chloride gas. Solvents can be used dependent upon the nature of the blocking group removal. For example, alcohols can be used for hydrogenation and diethyl ether for cleavage using hydrogen chloride gas. Reaction temperatures may vary from 0° C. to the boiling point of the respective solvent and reaction times of from 10 minutes to 48 hours. The preferred procedure when tert-butoxycarbonyl is the blocking group is to saturate a diethyl ether solution with hydrogen chloride and leave overnight at room temperature to yield the aminoacid hydrochloride which can be purified by recrystallization from ethanol on addition of diethyl ether.

The 1-fluorinated-2-amino-4-pentene reactants can be prepared by reduction followed by hydrolysis in manner known per se of an addition product of the corresponding fluorinated acetonitrile with an organo-metallic reagent, e.g. allyl magnesium bromide, chloride or iodide. Usually, the addition product will be reacted without isolation from the other products of the addition process. The reduction and hydrolysis conveniently can be carried out using water, methanol, ethanol or a mixture thereof and sodium borohydride at a temperature in the range $-78°$ C. and 0° C. for a period in the range 10 minutes to 24 hours. Preferably, a water/methanol mixture is used for a period of 1 hour. These reaction steps can be represented as follows:

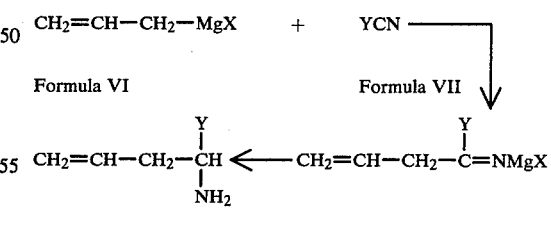

In Formulae VII, VIII and IX, Y is $FCH_2-$ or $F_2CH-$ and in Formulae VI and VIII, X represents bromine, chlorine or iodine.

The fluorinated aminopentene of Formula IX can be separated from the reduction product mixture by acidification with mineral acid, removal of neutral by-products by solvent, for example diethyl ether, extraction, and subsequent addition of alkali followed by solvent extraction with, for example, diethyl ether or chloroform and evaporation to yield the fluorinated aminopentene.

The allyl Grignard reactants of Formula VI can be prepared in manner known per se from the corresponding allyl halides and magnesium turnings using a solvent such as diethyl ether or tetrahydrofuran. The required fluorinated acetonitrile can be added to the resultant Grignard solution to form the required addition products. The fluorinated acetonitrile can be added as a solution in, for example, diethyl ether or tetrahydrofuran. Alternatively, in the case of mono-fluoro-acetonitrile, it can be added without a solvent whilst in the case of difluoro-acetonitrile, it can be added as a gas. During the addition, the reaction mixture conveniently is maintained at a temperature in the range $-78°$ C. and $0°$ C. and stirring is continued for a period of 10 minutes to 24 hours following the addition. Preferably, the reaction temperature is about $-20°$ C. and the reaction time is about 1 hour.

The reaction sequence commencing from an allyl halide described above is especially preferred for the preparation of beta-monofluoromethyl betaalanine.

Fluorinated aminopentenes of Formula IX also can be prepared in manner known per se by subjecting the corresponding 2-fluorinated methyl-4-pentenoic acid of the following Formula X to a Curtius Reaction or a Schmidt Reaction.

Formula X

In Formula X, Y is $FCH_2-$ or $F_2CH-$. This procedure is especially preferred for the preparation of beta-difluoromethyl beta-alanine.

The Curtius Reaction is described in, for example, Organic Reactions Vol III at page 338 and is well known per se for converting an acid to an amine via the corresponding acyl azide and isocyanate. In particular, the free acid of Formula X can be treated with a thionyl halide, preferably thionyl chloride, at reflux temperatures for about 1 to 4 hours or the sodium salt of the acid can be treated with oxalyl chloride in benzene or other aprotic solvent to give the corresponding acid chloride. The acid chloride can be treated with sodium azide at reflux temperature for about 40 to 100 hours followed by acid hydrolysis using a strong mineral acid, for example, hydrochloric acid or sulfuric acid or an organic acid such as p-toluenesulfonic acid for about 1 to 24 hours at reflux temperature to yield the required amine in the form of an acid addition salt. Alternatively, sodium azide can be added at room temperature to a solution of the acid chloride in a suitable solvent, for example acetone, and the mixture stirred for about 1 hour to form the azide. The acyl azide is extracted with, for example, diethylether, dried and the solvent evaporated in vacuo the acyl azide then is dissolved in a suitable solvent, for example benzene, the solution heated at reflux temperature for about 12 hours, and the solvent evaporated in vacuo to yield the isocyanate which is then treated with an alcohol, especially tert-butyl alcohol, to form the required amine in the form of its alkoxycarbonyl blocked derivative of Formula V.

The Schmidt Reaction is described in, for example, Organic Reactions Vol III at page 308 and is also well known per se for converting an acid into an amine by reaction with hydrazoic acid. In particular, the free acid of Formula X can be treated with hydrazoic acid for about 1 to 24 hours at temperatures of about $0°$ to $60°$ C. and in the presence of a strong mineral acid.

The fluorinated methylpentenoic acids of Formula X can be prepared in manner known per se by hydrolysis and decarboxylation of a corresponding fluorinated alkylated malonic acid dialkylester of the following Formula XI.

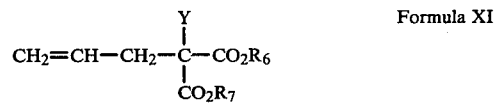

Formula XI

In Formula XI, Y is $FCH_2-$ or $F_2CH-$ and $R_6$ and $R_7$ independently represent $C_1-C_4$ alkyl groups. Each alkyl group $R_6$ and $R_7$ can be straight or branched chain and examples of suitable alkyl groups are methyl, ethyl, n-propyl, iso-propyl, n-butyl and, preferably, tert-butyl.

Hydrolysis and decarboxylation of the fluorinated diesters of Formula XI can be carried out by treatment with a strong mineral acid, for example, hydrochloric or sulfuric acid or a strong organic acid, for example, p-toluenesulfonic acid or trifluoroacetic acid at temperatures of from about $25°$ C. to $180°$ C. for about $\frac{1}{2}$ hour to 48 hours. When both $R_6$ and $R_7$ are tert-butyl, it is preferred that trifluoroacetic acid is used. However, when only $R_6$ represents tert-butyl, it is preferred that the fluorinated diester of Formula XI is treated with trifluoroacetic acid at about $25°$ C. for one hour and concentrated under reduced pressure to give the corresponding malonic acid monoester derivative having the Formula XII.

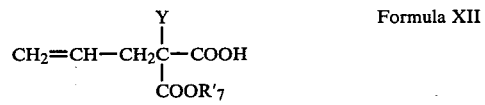

Formula XII wherein Y is $FCH_2-$ or $F_2CH-$ and $R_7'$ is $C_1-C_4$ alkyl excepting tertiary butyl. The monoester derivative of Formula XII is decarboxylated by treatment with an organic acid, for example, acetic acid or propionic acid at temperatures of about $100°$ to $160°$ C. for about 1 to 24 hours. It is preferred that the monoester derivative be decarboxylated by treatment with acetic acid at about $130°$ C. for 12 hours followed by concentration under reduced pressure to give the corresponding fluorinated 2-methyl-4-pentenoic acid alkyl ester which is hydrolyzed using a strong mineral acid, for example, hydrochloric acid or sulfuric acid or an organic acid, such as, p-toluenesulfonic acid or trifluoro acetic acid in water at temperatures up to the reflux temperature of the solvent for about 1 to 24 hours.

The fluorinated diesters of Formula XI can be prepared by fluoromethylation of the corresponding alkylated malonic acid diester of the following general Formula XIII

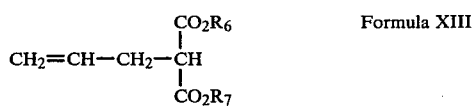

Formula XIII

In Formula XIII, $R_6$ and $R_7$ independently are $C_1-C_4$ alkyl. The fluoromethylation can be carried out in manner known per se by adding an excess of a fluoromethylating agent of the formula YW, where Y is FCH$_2$- or F$_2$CH- and W represents chlorine, bromine or iodine, to a solution in an aprotic solvent of a carbanion of the compound of Formula XIII. The reaction can be performed by stirring at a temperature in the range −70° to +80° C., preferably about 25° C., for a period of 15 minutes to 48 hours and the fluoromethylated product of Formula XI can be extracted from the reacted mixture by an organic solvent, such as diethylether or methylene chloride. The carbanion can be obtained in manner known per se by reacting the compound of Formula XIII in the aprotic solvent with a base, such as sodium hydride, potassium hydride, lithium acetylide, lithium carbide, lithium amide, sodamide, potassium tert-butoxide, lithium or sodium hexamethyldisalazane, and lithium diisopropylamide at a temperature in the range 0° to 70° C. for a period of 1 to 24 hours. The aprotic solvent can be, for example, diethylether, dimethoxyethane diglyme, tetrahydrofuran, hexamethylphosphoric acid triamide, dimethylsulfoxide, dioxane, benzene and mixtures thereof.

The esters of Formula XIII can be prepared by alkylation of a dialkyl malonate of the following general Formula XIV with an alkylating agent of the following general Formula XV.

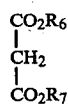  Formula XIV

  Formula XV

In Formula XIV, R$_6$ and R$_7$ independently are C$_1$–C$_4$ alkyl and in Formula XV, X' is a leaving group, preferably chlorine, bromine, tosyloxy, or methylsulfonyloxy. The alkylation can be carried out in manner known per se in a protic or aprotic solvent at a temperature in the range −30° C. to reflux temperature for a period of 30 minutes to 24 hours using any strong base which will abstract a proton from the malonate of Formula XIV. Suitable bases include sodium hydride, potassium hydride, lithium acetylide, lithium carbide, sodamide, lithium amide, lithium and sodium hexamethyldisalazane, sodium or potassium alkoxide such as methoxide, ethoxide, or tert-butoxide, or sodium or potassium hydroxide. Suitable solvents include the aprotic solvents diethylether, hexamethylphosphorus triamide, dimethylsulfoxide or tetrahydrofuran and the protic solvents methanol, ethanol, tert-butanol and ethylene glycol. As well known in the art, the actual base employed is dependent upon the nature of the solvent. Usually the malonate reactant, ester reactant and base will be used in the molar ratio of 1:1.1:1.5.

Beta-monofluoromethyl beta-alanine and beta-difluoromethyl beta-alanine also can be prepared by subjecting a fluorinated methylbutanedioic acid monoester of the following general Formula XVI to a Curtius or Schmidt Reaction (supra) to convert the free acid group into an amine and to hydrolyse the ester group to a free acid.

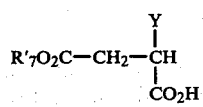  Formula XVI

In Formula XVI, Y is FCH$_2$- or F$_2$CH- and R$_7'$ is C$_1$–C$_4$ alkyl except tertiary butyl.

The monoester of Formula XVI can be prepared by selective hydrolysis and decarboxylation in manner known per se of a fluorinated malonic acid ditert-butyl ester derivative of the following general Formula XVII

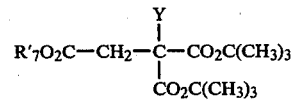  Formula XVII

In Formula XVII, Y is FCH$_2$— or F$_2$CH- and R$_7'$ is C$_1$–C$_4$ alkyl except tertiary butyl. Preferably, the hydrolysis is performed with trifluoroacetic acid at a temperature of about 25° C. for about ½ hour to 24 hours.

The ester derivative of Formula XVII can be prepared by an analagous process to that described above for preparing diesters of Formula XI but commencing with ditert-butyl malonate and an acetic acid derivative of the following general Formula XVIII.

  Formula XVIII

In Formula XVIII, R$_7'$ is C$_1$–C$_4$ alkyl except tertiary butyl and X' is a leaving group, preferably chlorine, bromine, tosyloxy or methylsulfonyloxy.

The ester amide derivatives of beta-monofluoromethyl beta-alanine and beta-difluoromethyl beta-alanine can be prepared directly or indirectly in manner known per se from said fluorinated methyl beta-alanines by for example esterification, amidation or N-acylation after, if necessary, protecting any functional group not involved in the desired reaction.

The amides of the invention in which the amide group is derived from the amine group usually will be prepared by N-acylation of the corresponding compound of the invention having a primary amino group using an acid halide, preferably the chloride or bromide.

In terms of producing a compound of Formula I, the acid halide will have the Formula R$_8$CO halogen wherein R$_8$ is C$_1$–C$_4$ alkyl, phenyl or phenyl(C$_1$–C$_4$ alkyl). Conveniently the reaction is conducted in water in the presence of a base such as sodium hydroxide or triethylamine at a temperature of from 0° C. to 25° C. for from ½ hour to 6 hours.

In the case where the said amide has an aminocarboxylic acid residue, the amide usually will be prepared by N-acylating the corresponding C$_1$–C$_4$ alkyl ester of the invention having a primary amino group with the corresponding aminocarboxylic acid or an anhydride thereof in which acid or anhydride the amino group is protected with a suitable blocking group such as benzyloxycarbonyl or tert-butoxycarbonyl. Conveniently the reaction is conducted in an ether, such as, tetrahydrofuran or dioxane, methylene chloride or chloroform and in the presence of a dehydrating agent when the free acid is employed, at a temperature of from about 0° C. to 35° C. for about 1 to 12 hours followed by acid hydrolysis to remove the protecting groups.

The esters of the invention usually will be prepared by treating the corresponding acid, for example with thionyl chloride, to form an acid halide which is then reacted with an alcohol at about 25° C. for from about 4 to 12 hours.

The amides of the invention in which the amide group is derived from the acid group usually will be prepared by acylation with an amine of a corresponding acid halide, for example, an acid chloride, or of the corresponding acid after, if necessary, protecting any free amino group with a suitable protecting group, for example, carbobenzyloxy or tert-butoxycarbonyl. Conveniently an excess of amine is used in a suitable solvent such as methylene chloride, chloroform, dimethylformamide, ethers, for example tetrahydrofuran or dioxane, or benzene at about 25° C. for about 1 to 4 hours. Suitable amines are, for example, ammonia, or a compound which is a potential source of ammonia, for example, hexamethylenetetramine; primary amines, for example, methylamine, ethylamine, or n-propylamine; and secondary amines such as dimethylamine, diethylamine or di-n-butylamine. Following the acylation any amino protecting group is removed for example by treatment with acid, for example, hydrogen bromide in dioxane or by hydrogenolysis.

In the case where the said amide has an aminocarboxylic acid residue, the amide usually will be prepared by acylating the corresponding acid of the invention or an acid functional derivative thereof such as an acid anhydride after, if necessary, protecting any free amino group as described above with a $C_1$–$C_4$ alkyl ester of the corresponding aminocarboxylic acid. Conveniently, the acylation is conducted in an ether, such as, tetrahydrofuran or dioxane at 0° to about 50° C. for about 1 to 24 hours followed by, for example, acid hydrolysis to remove the protecting group. When the free acid is employed, the reaction is carried out using a dehydrating agent such as dicyclohexylcarbodiimide.

The individual optical isomers of the primary amines of the invention can be separated by using a (+) or (−) binaphthylphosphoric acid salt by the method of R. Viterbo et al., Tetrahedron Letters 48, 4617 (1971). Other resolving agents such as (+) camphor-10-sulfonic acid may also be employed. The individual optical isomers of the N-substituted compounds of the invention can be obtained as described herein for the racemate starting with the resolved amine.

The invention is further illustrated by the following Examples.

EXAMPLE 1

Beta-monofluoromethyl beta-alanine hydrochloride (a) 1-Fluoro-2-amino-4-pentene hydrochloride

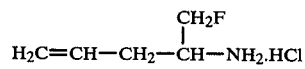

Allylmagnesiumbromide is prepared under an atmosphere of nitrogen, from 4.86 g (200 mmoles) of magnesium turnings, allylbromide (12.1 g, 100 mmoles) and dry ether (100 ml). The resultant Grignard solution is separated from the excess of magnesium, cooled to −20° C., and fluoroacetonitrile (5.31 g, 90 mmoles) in ether (50 ml) is added, dropwise, during about 30 minutes. The gummy pale-grey precipitate formed is stirred for an additional 30 minutes at −20° C., and then poured into a stirred mixture of methanol (200 ml), water (4 ml), and sodiumborohydride (3.8 g, 100 mmoles) cooled to −40° C. The transfer of the gummy precipitate is facilitated by rinsing the reaction flask with 200 ml of cold dry tetrahydrofuran. After stirring for 1 hour at −20° C. and 30 minutes at 0° C., the mixture is acidified with 3 N hydrochloric acid (about 50 ml) and evaporated. Water is added to the residue and the resultant mixture is extracted twice with ether to remove non-basic by-products, made alkaline with 4 N sodium hydroxide and extracted twice with ether again. After drying with sodium sulfate, dry hydrogen chloride gas is bubbled through the solution to form an oily precipitate (8.9 g) which is recrystallized from methanol/ether (6.8 g, 49%, mp. 124° C.).

Anal. Calcd for $C_5H_{11}NFCl$: C, 43.02; H, 7.94; N, 10.03. Found: C, 43.28; H, 7.83; N, 9.81.

NMR ($D_2O$): δ2.50 (2H, t, J=7 Hz), 3.70 (1H, m), 4.50 (2H, d of m, $J_{H-F}$=48 Hz), 5.65 (3H, m).

(b) 1-Fluoro-2-tert-butoxycarbonylamino-4-pentene

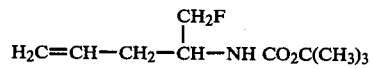

Tert-Butyloxycarbonyloxyimino-2-phenylacetonitrile (3.35 g, 13.6 mmoles) in dry tetrahydrofuran (40 ml) is slowly added with ice cooling to a stirred mixture of 1-fluoro-2-amino-4-pentene hydrochloride (1.9 g, 13.6 mmoles) and triethylamine (2.78 g, 27.2 mmoles) in tetrahydrofuran (30 ml). After standing overnight at room temperature, water is added, the tetrahydrofuran is removed under reduced pressure, and the residue is extracted twice with ether. After washing with 1 N sodium hydroxide, then with water until neutral, the organic layer is dried and stripped to give 1-fluoro-2-tert-butoxycarbonylamino-4-pentene (2.33 g, 85%) as an oil which is used without further purification.

NMR ($CDCl_3$): δ1.43 (9H, s) 2.30 (2H, t, J=7 Hz), 3.67 (1H, m) 4.35 (2H, d of m, $J_{H-F}$=47 Hz), 5.47 (3H, m).

(c) 4-Fluoro-3-tert-butoxycarbonylamino-1-butanoic acid

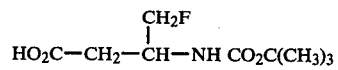

1-Fluoro-2-tert-butoxycarbonylamino-4-pentene (1.02 g, 5 mmoles), dissolved in glacial acetic acid (15 ml), is added to potassium permanganate (2.37 g, 15 mmoles) in water (75 ml), and kept overnight at room temperature. After destroying the excess of permanganate with 10% sodium bisulfite solution and saturating with sodium chloride, the mixture is extracted twice with ether. Evaporation gives 4-fluoro-3-tert-butoxycarbonylamino-1-butanoic acid (776 mg) as a white solid which on recrystallization from ether/petroleum ether affords 676 mg (61%) of pure material, m.p. 112°–112.5° C.

Anal. Calcd for $C_9H_{16}O_4NF$: C, 48.86; H, 7.29; N, 6.33. Found: C, 48.91; H, 7.16; N, 5.99.

NMR ($CDCl_3$): δ1.43 (9H, s), 2.65 (2H, d, J=6 Hz), 4.21 (1H, m), 4.45 (2H, d of m, $J_{H-F}$=47 Hz).

(d) Beta-monofluoromethyl beta-alanine hydrochloride

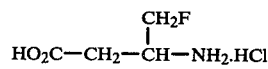

4-Fluoro-3-tert-butoxycarbonylamino-1-butanoic acid (545 mg, 2.46 mmoles) is dissolved in dry ether (20 ml) saturated with hydrogen chloride gas. After a few minutes, the solution becomes turbid and white crystals start to precipitate. Recrystallization from ethanol/ether afford beta-monofluoromethyl beta-alanine hydrochloride (265 mg, 68%), m.p. 152°–153° C. (dec).

Anal. Calcd for $C_4H_9O_2NFCl$: C, 30.49; H, 5.76; N, 8.89. Found: C, 30.48; H, 5.73; N, 8.88.

NMR (DCl/D$_2$O, 6 N): δ3.00 (2H, d, J=7 Hz), 4.10 (1, H, m), 4.83 (2H, d of m, $J_{H-F}$=46 Hz).

Beta-monofluoromethyl beta-alanine is obtained by dissolving the hydrochloride salt in ethanol, adding an equimolar amount of triethylamine, allowing the resultant solution to stand overnight (about 16 hours) at 4° C. and then filtering off the precipitate and recrystallizing from water by addition of ethanol.

EXAMPLE 2

Beta-difluoromethyl beta-alanine hydrochloride (a) 2-[1,1-Dimethylethoxy carbonyl] butanedioic acid 1-(1,1-dimethylethyl)-4-methylester

Di-tButyl malonate (10 mM,) is added, at room temperature under nitrogen, to a suspension of sodium hydride (11 mM, 55% dispersion in oil) in tetrahydrofuran (50 ml); after stirring for 1 hour, a solution of bromoacetic acid methyl ester (10 mM) in tetrahydrofuran (3 ml) is added drop-wise over a period of 10 minutes; stirring is continued for 48 hours. The mixture is then hydrolized, and extracted with ether. The organic layer is dried over anhydrous magnesium sulfate and concentrated in vacuo. The triester is isolated by distillation under reduced pressure, b.p.$_{0.5}$ 76°–78° C.

Anal. Calcd. for $C_{14}H_{24}O_6$: C, 58.32; H, 8.39. Found: C, 58.11; H, 8.11.

NMR (CDCl$_3$); δ1.43 (18H, s), 2.80 (2H, d, J=7 Hz) 3.61 (1H, t, J=7 Hz), 3.67 (4H, s).

(b) 2-Difluoromethyl-2-[1,1-dimethylethoxy carbonyl] butanedioic acid, 1-(1,1-dimethylethyl)-4-methyl ester

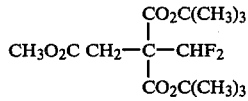

2-[1,1-Dimethylethoxycarbonyl] butanedioic acid, 1-[1,1-dimethylethyl]-methyl ester (1 mM,) is added at room temperature under nitrogen to a suspension of sodium hydride (5 mM, a 55% of dispersion in oil) in tetrahydrofuran (5 ml). After stirring and heating at 60° C. for 1 hour, a stream of chlorodifluoromethane is bubbled through the anion solution. Stirring and heating is continued for 18 hours. The mixture is hydrolyzed and extracted twice with ether. The organic layer is dried over anhydrous magnesium sulfate and concentrated to dryness. The desired product is isolated by a preparative chromatography on silica gel (eluent:ethyl acetate/hexane 2:8). m.p. 49°–50° C.

Anal. Calcd. for $C_{15}H_{24}F_2O_6$: C, 53.25; H, 7.15. Found: C, 53.70; H, 7.11.

NMR (CHCl$_3$) δ1.45 (18H, s), 3.00 (2H, s), 3.58 (3H, s), 6.26 (1H, t, $J_{HF}$=55 Hz)

(c) 2-Difluoromethyl butanedioic acid, 4-monomethyl ester

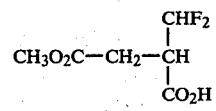

2-Difluoromethyl-2-(1,1-dimethylethoxy carbonyl) butanedioic acid, 1-(2,2-dimethylethyl)-4-methyl ester 3 (mM), is dissolved in trifluoroacetic acid (5 ml) at room temperature. After stirring for 1.5 hour at room temperature, the solvent is evaporated in vacuo yielding a white solid. The crude disubstituted malonic acid is taken off in glacial acetic acid (10 ml) and the mixture is heated at 100° C. for 12 hours. The solvent is evaporated in vacuo yielding a colourless oil which is distilled in vacuo, b.p.$_{0.6}$=95° C.

NMR (CDCl$_3$) δ2.70–3.00 (2H, m), 2.05–3.06 (1H, m), 3.67 (3H, s); 6.12 (1H, t of d, $J_{HF}$=54 Hz, $J_H$=3 Hz).

(d) 3-Difluoromethyl-4-chloro-4-oxo butanoic acid, methyl ester

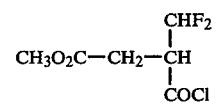

2-Difluoromethyl butanedioic acid, 4-monomethyl ester (2 mM,) is dissolved in thionyl chloride (10 ml) and the mixture is evaporated in vacuo yielding a yellowish oil.

(e) Beta-difluoromethyl beta-alanine hydrochloride

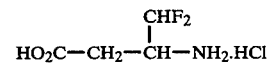

Sodium azide (1.1 eq) in water (1 ml) is added drop-wise at room temperature to the crude acyl chloride (2 mM) dissolved in acetone (5 ml). After 1 hour stirring at room temperature, the mixture is extracted with ether. The organic layer is dried over anhydrous magnesium sulfate and the solvent is evaporated in vacuo yielding a colourless oil. The crude acyl azide is dissolved in benzene and heated at reflux for 2 hours. The solvent is evaporated in vacuo yielding the expected isocyanate. The α-difluoromethyl isocyanate is dissolved in concentrated hydrochloric acid, and heated at 100° C. for 12 hours. The solvent is then evaporated in vacuo. The oil residue is taken off in water and decolorized with active charcoal. Filtration and evaporation of the solvent yielded beta-difluoromethyl beta-alanine hydrochloride as a white solid which is recrystallized from ethanol/diethyl ether. m.p. 150° C.

Anal. Calcd for $C_4H_8ClF_2NO_2$: C, 27.36; H, 4.59 N, 7.98. Found: C, 27.19; H, 4.50 N, 8.06.

NMR (D$_2$O) δ2.80–3.10 (2H, m), 3.75–4.60 (1H, m), 6.30 (1H, t of d, $J_{HF}$=53 Hz; $J_{HH}$=2 Hz).

Beta-difluoromethyl beta-alanine is obtained from its hydrochloride salt by dissolving the salt in water, adding 10% sodium hydroxide to render the aqueous solution neutral, saturating the aqueous layer with sodium chloride, extracting with diethylether, drying the extracts with anhydrous magnesium sulfate and evaporating the solvent in vacuo.

EXAMPLE 3

Beta-difluoromethyl beta-alanine hydrochloride (a) 2-(1,1-Dimethylethoxycarbonyl)-4-pentenoic acid, (1,1-dimethylethyl) ester $$CH_2=CH\text{-}CH_2\text{-}CH\ [CO_2C(CH_3)_3]_2$$

The procedure of Example 2(a) is substantially repeated using 3-bromo-1-propene instead of bromoacetic acid methyl ester to obtain the desired diester.

(b) 2-Difluoromethyl-2-(1,1-dimethylethoxycarbonyl)-4-pentenoic acid, (1,1-dimethyl-ethyl) ester

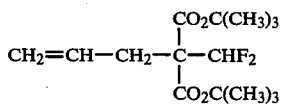

The procedure of Example 2(b) is substantially repeated commencing from the diester of Example 3(a) to yield the desired fluorinated diester.

(c) 2-Difluoromethyl 4-pentenoic acid

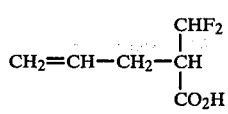

The procedure of Example 2(c) is substantially repeated commencing from the fluorinated diester of Example 3(b) to yield 2-difluoromethyl 4-pentenoic acid.

(d) 1,1-Difluoro-2-tert-butoxycarbonylamino-4-pentene

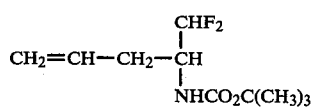

The procedures of Examples 2(d) and 2(e) are substantially repeated commencing from the acid of Example 3(c) except that the isocyanate is treated with tert-butyl alcohol yielding, 1,1-difluoro-2-tert-butoxy-carbonylamino-4-pentene.

(e) 4,4-Difluoro-3-tert-butoxy-carbonylamino-1-butanoic acid

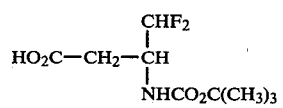

The procedure of Example 1(c) is substantially repeated commencing from the ester of Example 3(d) to yield the desired acid as a white solid.

(f) Beta-difluoromethyl beta-alanine hydrochloride

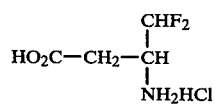

The procedure of Example 1(d) is substantially repeated commencing from the acid of Example 3(e) to yield, after recrystallization from ethanol/ether, beta-difluoromethyl beta-alanine hydrochloride identical with that obtained in Example 2.

EXAMPLE 4

3-Mono- and di-fluoromethyl-3-(1-oxo-ethylamino) propionic acid

To a solution of 2 mmole of beta-difluoromethyl beta-alanine in 5 ml of 1 N sodium hydroxide at 0° C. are added simultaneously from two syringes 160 mg of acetyl chloride diluted in 1 ml of dioxane and 2 ml of 1 N sodium hydroxide. After 30 minutes at 0° C. the solution is acidified by the addition of 6 N hydrochloric acid, then extracted well with dichloromethane. The organic phase is dried and concentrated to afford 3-difluoromethyl-3-(1-oxo-ethylamino) propionic acid.

The above procedure is repeated commencing from beta-monofluoromethyl beta-alanine to obtain 3-monofluoromethyl-3-(1-oxo-ethylamino) propionic acid.

EXAMPLE 5

3-Benzyloxycarbonyl-amino-3-mono- and di-fluoromethyl propionic acids

To a solution of 2 mmole of beta-difluoromethyl beta-alanine in 5 ml of 1 N sodium hydroxide at 0° C. are added simultaneously from two syringes 2 mmole of benzyl chloroformate in 1 ml of dioxane and 2 ml of 1 N sodium hydroxide. After 30 minutes at 0° C. the solution is acidified by the addition of 6 N hydrochloric acid, then extracted well with dichloromethane. The organic phase is dried and concentrated to afford 3-benzyloxycarbonyl-amino-3-difluoromethyl propionic acid.

The above procedure is repeated commencing from beta-monofluoromethyl beta-alanine to obtain 3-benzyloxycarbonyl-amino-3-monofluoromethyl propionic acid.

EXAMPLE 6

3-Amino-3-mono- and di-fluoromethyl-N-propylpropionamides hydrobromides

The difluoromethyl propionic acid of Example 5 is dissolved in 15 ml of dichloromethane and treated with 2 mmole of thionyl chloride at 25° C. for 1 hour after which 4 mmole of propyl amine is added. The solution is stirred at 25° C. for one hour, then washed with water, dried and concentrated. The residue is treated with 6 ml of a solution of dioxane containing 40% w/w hydrogen bromide and allowed to stand for 30 minutes at 25° C. after which 50 ml of ether is added. The resulting precipitate is collected to afford 3-amino-3-difluoromethyl-N-propyl-propionamide hydrobromide.

The above procedure is repeated commencing from the monofluoromethylpropionic acid of Example 5 to obtain 3-amino-3-monofluoromethyl-N-propylpropionamide hydrobromide.

EXAMPLE 7

3-Amino-3-mono- and di-fluoromethylpropionic acid ethyl esters

A solution of 2 mmole of beta-difluoromethyl beta-alanine in 15 ml of dichloromethane is treated with 2 mmole of thionyl chloride at 25° C. for one hour after which 20 ml of ethanol is added. The solution is stirred at 25° C. for one hour and concentrated to afford 3-amino-3-difluoromethylpropionic acid ethyl ester hydrochloride.

The procedure is repeated commencing from beta-monofluoromethyl beta-alanine to obtain 3-amino-3-monofluoromethyl propionic acid ethyl ester hydrochloride.

EXAMPLE 8

3-(2'-Aminopropionylamino)3-mono- and di-fluoromethylpropionic acids

A solution of 1 mmole of 3-amino-3-difluoromethylpropionic acid ethyl ester in 4 ml of methylene chloride is treated with 1 mmole of N-carbobenzoxyalanine and 1 mmole of N,N'-dicyclohexylcarbodiimide for 10 hours at 25° C. The mixture is cooled to 0° C. and the precipitated dicyclohexylurea filtered off. The filtrate is diluted with methylene chloride, washed with water, bicarbonate, dilute HCl, then dried and concentrated. The residue is treated with 5 ml of ethanol and 5 ml of a 40% (w/w) solution of hydrogen bromide in dioxane for 30 minutes at 25° C. Ether (50 ml) is added and the resulting precipitate collected which is treated with 15 ml of 1 N sodium hydroxide for 10 hours at 25° C. The pH of the solution is adjusted to neutral, and the product isolated from an Amberlite 120 H+ resin by elution with 2 M ammonium hydroxide affording 3-(2'-aminopropionylamino)-3-difluoromethylpropionic acid.

The above procedure is repeated commencing from 3-amino-3-monofluoromethyl propionic acid ethyl ester to obtain 3-(2'-aminopropionylamino)-3-monofluoromethyl propionic acid.

In the following Examples relating to pharmaceutical compositions, the term "active compound" is used to indicate the compound betadifluoromethyl beta-alanine. This compound may be replaced in these compositions by any other compound of the invention, for example by beta-monofluoromethyl beta-alanine. Adjustments in the amount of medicament may be necessary or desirable depending upon the degree of activity of the medicament as is well known in the art.

EXAMPLE 9

An illustrative composition for hard gelatin capsules is as follows:

| | | |
|---|---|---|
| (a) | active compound | 20 mg |
| (b) | talc | 5 mg |
| (c) | lactose | 90 mg |

The formulation is prepared by passing the dry powders of (a) and (b) through a fine mesh screen and mixing them well. The powder is then filled into hard gelatine capsules at a net fill of 115 mg per capsule.

EXAMPLE 10

An illustrative composition for tablets is as follows:

| | | |
|---|---|---|
| (a) | active compound | 20 mg |
| (b) | starch | 43 mg |
| (c) | lactose | 45 mg |
| (d) | magnesium stearate | 2 mg |

The granulation obtained upon mixing the lactose with the compound (a) and the part of the starch and granulated with starch paste is dried, screened, and mixed with the magnesium stearate. The mixture is compressed into tablets weighing 110 mg each.

EXAMPLE 11

An illustrative composition for an injectable suspension is the following 1 ml ampul for an intramuscular injection:

| | | weight percent |
|---|---|---|
| (a) | active compound | 1.0 |
| (b) | polyvinylpyrrolidone | 0.5 |
| (c) | lecithin | 0.25 |
| (d) | water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

EXAMPLE 12

| | mg/suppository |
|---|---|
| Active Compound | 50 |
| Oil of Theobroma | 950 |

The medicament is powdered and passed through a B.S. No. 100 Sieve and triturated with molten oil of Theobroma at 45° C. for form a smooth suspension. The mixture is well stirred and poured into moulds each of nominal 1 G capacity, to produce suppositories.

EXAMPLE 13

The following compounds were tested for inhibition of GABA-T activity:
(A) 4-mono-fluoro-4-amino-1-butanoic acid (see U.K. Patent Specification No. 2,005,264 A)
(B) 4-difluoromethyl-4-amino-1-butanoic acid (see U.K. Patent Specification No. 2,005,264 A)
(C) beta-monofluoromethyl beta-alanine
(D) beta-difluoromethyl beta-alanine
(E) 3-trifluoromethyl-3-amino-1-propionic acid (Formula I analogue; $R_1$=OH; $R_2$=H; Y=$CF_3$)

In an in vitro test, GABA-T purified from pig brain was incubated with each of the compounds A to E at a concentration of 1 mM. Except in the case of compound E, each compound showed a time-dependent inhibition of GABA-T. The times (in minutes) needed to inactivate 50% of GABA-T are given in Table 1 below.

In an in vivo test, each of compounds A, B, D and E were injected into mice to assess the time and dose dependent inhibition of GABA-T by the method of M. J. Jung et al (J. Neurochemistry, 28 (1977) at pages 717–723). The percentage reduction in brain GABA-T activity after 6 hours at certain specified doses are given in Table 1 below.

TABLE 1

$$HO_2C(CH_2)_m\underset{Y}{\overset{|}{C}}HNH_2 \quad \text{Formula XX}$$

| Compound | Formula XX | | In vitro 50% Inactivation (mins) | In vivo % Reduction after 6 hours |
|---|---|---|---|---|
| | m | Y | | |
| (A) | 2 | $CH_2F$ | 11.5 | 50% at 50 mg/kg |
| (B) | 2 | $CHF_2$ | 13.2 | Not tested |
| (C) | 1 | $CH_2F$ | 10.3 | 50% at 10 mg/kg |
| (D) | 1 | $CHF_2$ | 2 to 3 | 95% at 10 mg/kg |
| (E) | 1 | $CF_3$ | Inactive | Inactive at |

TABLE 1-continued $$\underset{\underset{Y}{|}}{HO_2C(CH_2)_mCHNH_2} \quad \text{Formula XX}$$

| Compound Formula XX | | In vitro 50% Inactivation (mins) | In vivo % Reduction after 6 hours 1000 mg/kg |
|---|---|---|---|
| m | Y | | |

Some further relevant information concerning the results of the in vivo test is given below under the appropriate heading identifying the relevant compound.

Compound A

At 500 mg/kg the residual GABA-T activity after 6 hours was 15%. Brain GABA levels were elevated in a dose dependent manner; the increase being four fold at 30 mg/kg and 8 fold at 250 mg/kg.

Compound B

Insufficient compound was available at the relevant time to perform the in vivo test in respect of this compound.

Compound C

At 200 mg/kg the residual GABA-T activity after 6 hours was between 12 and 15%. Brain GABA levels were elevated by 70% at the 10 mg/kg dose and 450% at 200 mg/kg. The maximum level of inhibition at each dose was reached after 6 hours and the level of inhibition was obtained for at least 48 hours (no longer time periods being measured).

Compound D

At 1 mg/kg the residual GABA-T activity after 6 hours was 60%. The onset of inhibition was more rapid than with Compounds A and C with the maximum inhibition being reached within 3 hours and maintained for at least 48 hours (no longer time periods being measured). The increase in brain GABA levels were three to four fold at 5 mg/kg and in excess of ten fold at 25 mg/kg.

The Compounds A to E were also tested by the method of C. Lamar (J. Neurochemistry, 17 (1970) at pages 165–170) to determine the extent of protection against mercapto propionic acid induced seizures. Compounds A to D were all effective in protecting against the seizures with Compound D being the most effective. At 5 mg/kg Compound D provided 100% protection 6 hours after injection and even after 24 hours provided 50% protection. However, in the case of Compound E, there was no protection against the seizures; indeed the seizures appeared to be potentiated.

The tests reported briefly above are a clear indication of the irreversible inhibition of GABA-T by compounds of the invention. Further they demonstrate the surprising nature of said inhibition in that the analogous known 3-trifluoro-3-amino-propionic acid is inactive in the tests and the activity is significantly greater than the corresponding immediately higher analogues.

We claim:

1. 3-amino-3-fluoromethylpropionic acid or a pharmaceutically acceptable salt thereof.

2. 3-amino-3-difluoromethylpropionic acid or a pharmaceutically acceptable salt thereof.

3. A pharmaceutical composition for use in increasing brain levels of GABA comprising an effective amount of 3-amino-3-fluoromethylpropionic acid or a pharmaceutically acceptable salt thereof and a pharmaceutically acceptable carrier or diluent.

4. A pharmaceutical composition for use in increasing brain levels of GABA comprising an effective amount of 3-amino-3-difluoromethylpropionic acid or a pharmaceutically acceptable salt thereof and a pharmaceutically acceptable carrier or diluent.

5. A composition as defined in claim 3 or 4 in unit dosage form containing 5 to 2000 mg of said active ingredient per unit dose.

6. A method of inhibiting γ-aminobutyric acid transaminase in a patient in need thereof which comprises administering to said patient an effective γ-aminobutyric acid transaminase inhibiting amount of 3-amino-3-fluoromethylpropionic acid or 3-amino-3-difluoromethylpropionic acid, or a pharmaceutically acceptable salt thereof.

7. A method of treating a patient having a disorder of the central nervous system function characterized in a low level of brain γ-aminobutyric acid which comprises administering an effective γ-aminobutyric acid transaminase inhibiting amount of 3-amino-3-fluoromethylpropionic acid or 3-amino-3-difluoromethylpropionic acid, or a pharmaceutically acceptable salt thereof.

8. A method as defined in claim 6 or 7 wherein the compound administered is 3-amino-3-fluoromethylpropionic acid or a pharmaceutically acceptable salt thereof.

9. A method as defined in claim 6 or 7 wherein the compound administered is 3-amino-3-difluoromethylpropionic acid or a pharmaceutically acceptable salt thereof.

* * * * *